United States Patent [19]

Kang et al.

[11] Patent Number: 5,338,854

[45] Date of Patent: * Aug. 16, 1994

[54] FLUORESCENT FATTY ACIDS DERIVED FROM DIPYRROMETHENEBORON DIFLUORIDE DYES

[75] Inventors: Hee C. Kang; Richard P. Haugland, both of Eugene, Oreg.

[73] Assignee: Molecular Probes, Inc., Eugene, Oreg.

[*] Notice: The portion of the term of this patent subsequent to Dec. 28, 2010 has been disclaimed.

[21] Appl. No.: 654,881

[22] Filed: Feb. 13, 1991

[51] Int. Cl.⁵ .................... H01S 3/20; C07D 207/44; C07F 5/02
[52] U.S. Cl. .................... 548/110; 548/405
[58] Field of Search ................ 548/405, 110

[56] References Cited

U.S. PATENT DOCUMENTS

| | | | |
|---|---|---|---|
| 4,774,339 | 9/1988 | Haugland | 548/405 |
| 4,916,711 | 4/1990 | Boyer et al. | 372/53 |
| 5,187,288 | 2/1993 | Kang | 548/405 |
| 5,248,782 | 9/1993 | Haugland | 548/405 |
| 5,262,545 | 11/1993 | Haugland | 548/405 |
| 5,274,113 | 12/1993 | Kang | 548/405 |

OTHER PUBLICATIONS

Roberts, "Basic Principles of Organic Chemistry", pp. 65–66 (1964).
Falk, Monat. Chem., 110, 987 (1979).
Waggoner et al., *Fluorescent Probes of Biological Membrances,* Proc. Natl. Acad. Sci., 67, 579 (1970).
de Bony et al., *Transverse and Lateral Distribution of Phospholipids and Glycolipids in the Membrane of the Bacterium Micrococcus luteus,* Biochem. 28, 3728 (1989).
Galla et al., *Chemically Induced Phase Separation in Mixed Vesicles Containing Phosphatidic Acid. An Optical Study,* J. Am. Chem. Soc., 97, 4114 (1975).
Shinitzky et al., *Microviscosity and Order in the Hydrocarbon Region of Micelles and Membranes Determined with Fluorescent Probes. I. Synthetic Micelles,* Biochem., 10, 2106 (1971).

(List continued on next page.)

*Primary Examiner*—Mark L. Berch
*Attorney, Agent, or Firm*—Allegra J. Helfenstein

[57] ABSTRACT

This invention relates to improved fluorescent fatty acid analogs derived from dipyrrometheneboron difluoride ("BDY") dyes that absorb light at wavelengths longer than 480 nm. The BDY fluorophore or a derivative thereof is incorporated at various locations along the alkyl portion of the fatty acid ("BDY fatty acid"). The general formula of a BDY fatty acid is as follows:

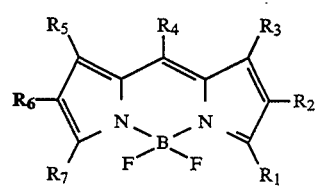

wherein at least one of the substituents $R_1$, $R_2$, $R_3$, $R_4$, $R_5$, $R_6$ and $R_7$ is a carboxylic acid terminated alkyl residue containing 5 to 22 carbon atoms. The remaining substituents, singly or in any combination, are: additional alkyl or arylalkyl residues containing 1 to 16 aliphatic carbon atoms, or aryl or heteroaryl residues, or hydrogen. Symmetrically substituted BDY fluorophores are conveniently synthesized from a single pyrrole precursor in a "one-pot" reaction. Alternatively, BDY fatty acids are synthesized from two different pyrrole precursors. The combination of fatty acids with these electrically neutral, photostable, strongly colored, and mostly highly fluorescent BDY dyes having relatively narrow absorption and emission spectra results in an improved fluorescent probe particularly useful for studying natural and synthetic lipid membranes and related areas.

20 Claims, 2 Drawing Sheets

FLUORESCENT FATTY ACIDS DERIVED FROM DIPYRROMETHENEBORON DIFLUORIDE DYES

This invention was made with government support under grants number GM 37347 awarded by the National Institutes of Health. The government has certain rights in this invention.

FIELD OF THE INVENTION

This invention relates to improvements in fluorescent fatty acids, particularly to fatty acid analogs derived from dipyrrometheneboron difluoride dyes (derivatives of 4,4-difluoro-4-bora-3a,4a-diaza-s-indacene dyes) that absorb light at wavelengths longer than 480 nm. The combination of fatty acids with these electrically neutral, photostable, strongly colored, and mostly highly fluorescent dyes having relatively narrow absorption and emission spectra results in an improved fluorescent probe particularly useful for studying natural and synthetic lipid membranes and related areas.

BACKGROUND OF THE INVENTION

Fluorescent fatty acids and derivatives of fluorescent fatty acids are examples of what are usually termed fluorescent probes. A fatty acid is a hydrocarbon chain terminating in a carboxylic acid. The hydrocarbon chain may be completely saturated or may contain one or more double bonds; the chain may be linear or branched. A fluorescent probe is a fluorescent compound used to "probe" structures and/or processes at the molecular and cellular level, by mimicking the natural compound. Fluorescent probes have been extensively utilized in biological and biomedical research both to visualize sites and for quantitative measurements. Fluorescent probes have also been used in electronics, polymer chemistry, medicine, forensics, and other diverse areas.

Fluorescent fatty acids have been used as probes for membrane and liposome structure and biological properties, for biosynthetic incorporation into cells, and in Langmuir-Blodgett films, etc. Fluorescent fatty acids have been synthetically incorporated into triglycerides, phospholipids, cholesteryl esters, phorbols, sphingolipids, and coenzyme A. Such synthetic products from fluorescent fatty acids have applications as probes similar to the fluorescent free fatty acids. The synthetic product to which the fluorescent fatty acid is attached, however, may also confer ability to specifically interact with a receptor site. This site may be a binding site on a cell, an enzyme, a polymer or other structure. The presence of the fluorophore as part of the probe may permit detection or quantitation of binding to the receptor, following the kinetics of an enzyme-catalyzed reaction, measurement of properties of the site to which the probe is bound, or visualization of substrates to which the probe is bound.

Fluorescence useful for such applications is generally initiated by absorption of light from an external, relatively concentrated light source. The sensitivity of these applications is improved by having dyes that have high absorbance of the exciting light and high fluorescence quantum yield. The applications are furthermore improved by having dyes that resist photobleaching by the exciting light and that have spectral wavelengths in a range that avoids the background from contaminants that may be present in the samples.

Certain lasers are particularly useful as a concentrated light source for the excitation of fluorescence. These include the argon laser with principal output at 488 nm and 514 nm; helium-neon lasers that can be selected to have maximum output at either 543 nm, 594 nm, or 633 nm; the krypton laser which has significant output at 568 nm and 647 nm; and laser diodes, which are commonly available at this time, with output above 660 nm. The argon laser is extensively used in such techniques as flow cytometry and laser scanning microscopy, which are two areas in which this invention has applications.

A number of dyes have previously been found to be fluorescent, however many of these dyes have characteristics which interfere with their usefulness. For example, many known fluorescent dyes do not have significant absorbance at the desired excitation wavelengths, or are significantly quenched in aqueous solution or are unstable during the illumination.

Fluorescent analogs of fatty acids have been described previously. Among those described are those derived from the fluorescent compounds anthracene (Waggoner and Stryer, *Fluorescent Probes of Biological Membranes*, PROC. NATL. ACAD. SCI. 67, 579 (1970) and Bony, Lopez, Gilleron, Welby, et.al., *Transverse and Lateral Distribution of Phospholipids and Glycolipids in the Membrane of the Bacterium Micrococcus luteus*, BIOCHEM. 28, 3728 (1989)), pyrene (Galla & Sackmann, *Chemically Induced Phase Separations in Mixed Vesicles Containing Phosphatidic Acid. An Optical Study*, J. AM. CHEM. SOC. 97, 4114 (1975)), perylene (Shinitzky, Dianoux, Gitler & Weber, *Microviscosity and order in the mydrocarbon region of micelles and membranes determined with fluorescent probes. I. Synthetic micelles*, BIOCHEM. 10, 2106 (1971)), naphthalene (Lee et.al., *Interaction of Fatty Acids with the Calcium-Magnesium Dependent Adenosine Triphosphatase from Sarcoplasmic Reticulum*, BIOCHEM. 21, 6441 (1982)), carbazole (Omann & Lakowicz, *Interactions of Chlorinated Hydrocarbon Insecticides with Membranes*, BBA 684, 83 (1982)), and nitrobenzoxadiazole (NBD) (Derzko & Jacobson, *Comparative Lateral Diffusion of Fluorescent Lipid Analogues in Phospholipid Multibilayers*, BIOCHEM. 19, 6050 (1980)).

Of these fluorescent fatty acids that have been described previously, only the NBD analogs have absorption maxima above 450 nm. The NBD derivatives have maximum absorption at 460 to 480 nm. Long wavelength absorbance usually increases the utility of a fluorescent probe since it reduces the interference from cellular autofluorescence and reduces the cytotoxic effect of the fluorophore in combination with light. Furthermore, absorbance at 488 or 514 nm permits use of the principal output of the argon laser to effect excitation of the probe.

Known fluorescent fatty acids have other disadvantages as well. Fluorescence of NBD derivatives, for example, is highly dependent on the environment. The NBD fluorophore also tends to fold back to the aqueous interface in cell membranes and liposomes. See Chattopadhyay & London, *Spectroscopic and Ionization Properties of N-(7-nitrobenz-2-oxa-1,3-diazol-4-yl)-Labeled Lipids in Model Membranes*, BIOCHIM. BIOPHYS. ACTA 938, 24 (1988). Other long-wavelength fluorophores such as fluoresceins, rhodamines, carbocyanines, oxonols, and most oxazines have electronic charges at pH 7 which usually preclude their use as lipophilic fluorescent probes because the fluorophore is not readily incorporated into the lipophilic environment of the membrane.

What is needed is an improved fatty acid analog. Dipyrrometheneboron difluoride ("BDY") dyes contribute many desirable characteristics to the fatty acid analogs. Longer wavelength fatty acids derived from BDY, which are the subject of this invention, extend the useful excitation wavelengths from near 500 nm to beyond 600 nm. The BDY fluorophore is electrically neutral and lipophilic, which properties permit it to be solubilized better in non-polar solvents and cell membranes. The BDY fluorophore also has significantly higher absorbance and fluorescence yield than any of the other fluorophores that have been used to prepare fluorescent fatty acids. The BDY fatty acids are also highly colored and may be detected without utilizing the fluorescent characteristic.

Simple alkyl derivatives of the BDY fluorophore, 4,4-difluoro-4-bora-3a,4a-diaza-s-indacene, have been described by Treibs & Kreuzer, *Difluorboryl-komplexe von diund tripyrrylmethenen*, LIEBIGS ANNALEN CHEM. 718, 203 (1968) and by Worries, Kopek, Lodder, & Lugtenburg, *A novel water-soluble fluorescent probe: Synthesis, luminescence and biological properties of the sodium salt of the 4-sulfonato-3,3',5,5'-tetramethyl-2,2'--pyrromethen-1,1'-BF₂ complex*, RECL. TRAV. CHIM. PAYS-BAS 104, 288 (1985) as being highly fluorescent with spectral properties that are similar to fluorescein with maximum absorbance at about 490 to 510 nm and maximum emission at about 500 to 530 nm. U.S. Pat. No. 4,774,339 to Haugland et al. (1988) ('339 patent) describes BDY dyes that contain reactive groups suitable for conjugation to biomolecules, that have good photostability, and which have fluorescein-like spectra. Heteroaryl-Substituted Dipyrrometheneboron Difluoride Dyes and Methods for Their Synthesis are described in co-pending application filed by inventors Haugland and Kang on Dec. 18, 1990 ("heteroaryl application"). Neither the earlier references nor the '339 patent nor the heteroaryl application disclose nor suggest the subject BDY fatty acids with long wavelength fluorescence properties, nor the use of BDY dyes to form fatty acid analogs.

It is the object of this invention to provide novel fluorescent fatty acid analogs useful as probes, and methods for their synthesis. It is a further object of this invention to provide novel fluorescent fatty acids derived from the BDY fluorophore.

SUMMARY OF THE INVENTION

This invention describes novel fatty acid analogs in which the BDY fluorophore or a derivative thereof is incorporated at various locations along the alkyl portion of a fatty acid ("BDY fatty acid"), and methods for the synthesis of such analogs. The general formula of a BDY fatty acid is as follows:

wherein at least one of the substituents $R_1$, $R_2$, $R_3$, $R_4$, $R_5$, $R_6$ and $R_7$ is a carboxylic acid terminated alkyl residue containing 5 to 22 carbon atoms. The alkyl residue is saturated or unsaturated, linear or branched. The remaining substituents, singly or in any combination, are additional alkyl or arylalkyl residues containing 1 to 16 aliphatic carbon atoms, or aryl or heteroaryl residues, or hydrogen.

In general, there are two synthetic routes to the BDY fatty acids from pyrrole precursors, depending on whether the final product is symmetric or asymmetric. Symmetrically substituted BDY fluorophores are conveniently synthesized from a single pyrrole precursor in a "one-pot" reaction. Alternatively, BDY fatty acids are synthesized from two different pyrrole precursors.

DETAILED DESCRIPTION OF THE EMBODIMENTS

This invention describes novel fatty acid analogs derived from dipyrrometheneboron difluoride (4,4-difluoro-4-bora-3a,4a-diaza-s-indacene) dyes (BDY fatty acids) and methods for their synthesis. The BDY fatty acids generally have the structure:

wherein at least one of the substituents $R_1$, $R_2$, $R_3$, $R_4$, $R_5$, $R_6$ and $R_7$ is an alkyl residue, where the alkyl residue contains 5 to 22 carbon atoms and is terminated by a carboxylic acid. The carboxylic acid terminated residue is linear or branched, and saturated or unsaturated. In other words, the residue is a linear hydrocarbon chain that is fully saturated or is unsaturated; or contains one or more branches, again being saturated or unsaturated.

The remaining substituents of $R_1$, $R_2$, $R_3$, $R_4$, $R_5$, $R_6$ and $R_7$, which may be the same or different, are: additional alkyl or arylalkyl residues, or aryl or heteroaryl residues, or hydrogen. The additional alkyl or arylalkyl residues contain 1 to 16 carbon atoms exclusive of any aromatic ring structures, i.e. the residues contain 1 to 16 aliphatic carbon atoms. An aryl residue contains an aromatic ring structure. A ring can be a 5- or 6- member ring. The ring structure can be a single ring structure or a fused two-ring structure. A heteroaryl residue is an aromatic ring structure that contains at least one heteroatom (a non-carbon atom forming the ring structure). The heteroaryl residue can contain one or more heteroatoms.

The aryl residue(s) are preferably phenyl or naphthyl or lower alkyl or alkoxy-substituted phenyl or naphthyl. Preferred heteroaryl residues include pyrrole, thiophene, furan, oxazole, isoxazole, oxadiazole, imidazole, benzoxazole, benzothiazole, benzimidazole, benzofuran and indole.

In a preferred embodiment of the invention, at least one and no more than two of the substituents $R_1$, $R_2$, $R_3$, $R_4$, $R_5$, $R_6$ and $R_7$ is/are a carboxylic acid terminated alkyl residue containing 5 to 22 carbon atoms, and the remaining five or six substituents are, singly or in combination: additional alkyl or arylalkyl residues containing 1 to 16 aliphatic carbon atoms, or aryl or heteroaryl residues, or hydrogen.

In a further embodiment of the invention, the substituents are symmetrical, e.g. $R_1=R_7$, $R_2=R_6$, or $R_3=R_5$. The symmetry may be partial, i.e. $R_1=R_7$, $R_2=R_6$, or $R_3=R_5$; or the symmetry may be complete, i.e. $R_1=R_7$, $R_2=R_6$, and $R_3=R_5$. In the symmetrical fatty acid analogs, the carboxylic acid terminated residue(s) can be located at symmetrical positions or at the $R_4$ position. The carboxylic acid terminated alkyl residues can be linear or branched, saturated or unsaturated.

The novel BDY fatty acid analogs have been biosynthetically incorporated into living fibroblast cells. The experimentally incorporated fatty acid analogs were those in which the combined number of carbons in the linear portion of at least two hydrocarbon chains equaled or exceeded about thirteen. In other words, where the number of carbons in the carboxylic acid terminated alkyl residue equaled n, the number of carbons in the linear portion of the additional alkyl or arylalkyl residue equaled about 13-n (in the case where the combination equaled thirteen). Incorporation was more readily achieved where the carboxylic acid terminated residues contained more than about 8 carbons.

Table 1 contains a sample of representative BDY fatty acids. The examples are representative compounds only and are not intended to be exclusive. Tables 2 and 3 contain characteristics of the representative compounds.

TABLE 2

PHYSICAL PROPERTIES OF BDY FATTY ACID DERIVATIVES

| # | M.P. (°C.) | $ABS_{max}^{\dagger}$ (nm) | $EM_{max}^{\dagger}$ (nm) | $R_f$ | T.L.C. Solvent |
|---|---|---|---|---|---|
| 1 | 64–66 | 504.8 | 511 | 0.48 | Solvent A |
| 2 | 103–104 | 507.6 | 514 | 0.36 | Solvent A |
| 3 | 77–78 | 508.8 | 515 | 0.38 | Solvent A |
| 4 | 81–82 | 508.8 | 515 | 0.46 | Solvent A |
| 5 | 96–98 | 509.2 | 516 | 0.41 | Solvent A |
| 6 | 162–163 | 494.4 | 504 | 0.40 | Solvent A |
| 7 | 78–80 | 504.8 | 512 | 0.44 | Solvent A |
| 8 | oil | 533.6 | 551 | 0.40 | Solvent A |
| 9 | oil | 558.8 | 568 | 0.36 | Solvent A |
| 10 | 83 (dec) | 508.0 | 515 | 0.30 | Solvent A |
| 11 | 50–52 | 511.2 | 517 | 0.54 | $CHCl_3$ |
| 12 | 62–63 | 512.4 | 516 | 0.36 | $CHCl_3$ |
| 13 | 33–35 | 508.8 | 515 | 0.42 | $CHCl_3$ |
| 14 | oil | 508.8 | 515 | 0.25 | $CHCl_3$ |
| 15 | 58–59 | 508.0 | 516 | 0.38 | $CHCl_3$ |
| 16 | 75–77 | 494.8 | 507 | 0.41 | $CHCl_3$ |
| 17 | 65–67 | 504.8 | 512 | 0.35 | $CHCl_3$ |
| 18 | oil | 533.6 | 552 | 0.55 | $CHCl_3$ |
| 19 | 52–53 | 558.8 | 568 | 0.43 | $CHCl_3$ |
| 20 | oil | 504.8 | 513 | 0.60 | Solvent A |
| 21 | 135 (dec) | 509.6 | 516 | 0.15 | Solvent A |
| 22 | 45–46 | 509.6 | 515 | 0.38 | Solvent A |
| 23 | oil | 509.2 | 516 | 0.25 | $CHCl_3$ |
| 24 | oil | 509.2 | 515 | 0.83 | $CHCl_3$ |
| 25 | oil | 508.4 | 515 | 0.70 | $CHCl_3$ |
| 26 | 79–81 | 508.8 | 515 | 0.71 | $CHCl_3$ |
| 27 | oil | 508.0 | 515 | 0.14 | $CHCl_3$ |

†Absorption and emmision spectra were measured in methanol solvent
Solvent A = 10% methanol in chloroform

TABLE 1

EXAMPLES ‡ OF BDY FATTY ACID DERIVATIVES

| # | $R_1$ | $R_2$ | $R_3$ | $R_4$ | $R_5$ | $R_6$ | $R_7$ |
|---|---|---|---|---|---|---|---|
| 1 | $(CH_2)_{11}CO_2H$ | H | H | H | $CH_3$ | H | $CH_3$ |
| 2 | $(CH_2)_{11}CO_2H$ | H | H | H | H | H | $CH_3$ |
| 3 | $(CH_2)_8CO_2H$ | H | H | H | H | H | $(CH_2)_3CH_3$ |
| 4 | $(CH_2)_4CO_2H$ | H | H | H | H | H | $(CH_2)_7CH_3$ |
| 5 | $(CH_2)_2CO_2H$ | H | H | H | H | H | $(CH_2)_9CH_3$ |
| 6 | $CH_3$ | H | $CH_3$ | $(CH_2)_8CO_2H$ | $CH_3$ | H | $CH_3$ |
| 7 | $(CH_2)_{15}CO_2H$ | H | H | H | $CH_3$ | H | $CH_3$ |
| 8 | $(CH_2)_{11}CO_2H$ | H | H | H | Ph* | H | Ph* |
| 9 | $(CH_2)_{11}CO_2H$ | H | H | H | H | H | Th* |
| 10 | $(CH_2)_9CO_2H$ | H | H | H | $CH_3$ | H | $CH_3$ |
| 11 | $(CH_2)_{11}CO_2CH_3$ | H | H | H | $CH_3$ | H | $CH_3$ |
| 12 | $(CH_2)_{11}CO_2CH_3$ | H | H | H | H | H | $CH_3$ |
| 13 | $(CH_2)_8CO_2CH_3$ | H | H | H | H | H | $(CH_2)_3CH_3$ |
| 14 | $(CH_2)_4CO_2CH_3$ | H | H | H | H | H | $(CH_2)_7CH_3$ |
| 15 | $(CH_2)_2CO_2CH_3$ | H | H | H | H | H | $(CH_2)_9CH_3$ |
| 16 | $CH_3$ | H | $CH_3$ | $(CH_2)_8CO_2CH_3$ | $CH_3$ | H | $CH_3$ |
| 17 | $(CH_2))_{15}CO_2CH_3$ | H | H | H | $CH_3$ | H | $CH_3$ |
| 18 | $(CH_2)_{11}CO_2CH_3$ | H | H | H | Ph* | H | Ph* |
| 19 | $(CH_2)_{11}CO_2CH_3$ | H | H | H | H | H | Th* |
| 20 | $(CH_2)_{10}OH$ | H | H | H | $CH_3$ | H | $CH_3$ |
| 21 | $(CH_2)_{11}CO_2H$ | H | H | H | H | H | $(CH_2)_{11}CO_2H$ |
| 22 | $(CH_2)_{11}CO_2H$ | H | H | H | H | H | $(CH_2)_{11}CO_2CH_3$ |
| 23 | $(CH_2)_{11}CO_2CH_3$ | H | H | H | H | H | $(CH_2)_{11}CO_2CH_3$ |
| 24 | $(CH_2)_9CH_3$ | H | H | H | H | H | $(CH_2)_9CH_3$ |
| 25 | $(CH_2)_7CH_3$ | H | H | H | H | H | $(CH_2)_7CH_3$ |
| 26 | $(CH_2)_3CH_3$ | H | H | H | H | H | $(CH_2)_3CH_3$ |
| 27 | $(CH_2)_8CO_2CH_3$ | H | H | H | H | H | $(CH_2)_8CO_2CH_3$ |

*Ph = Phenyl, Th = 2-Thienyl
‡Preferred representative compounds only, not intended to be exclusive

TABLE 3

$^1$H-NMR SPECTRAL DATA OF BDY FATTY ACID DERIVATIVES

| # | Chemical shift in ppm in CDCl$_3$ (300 MHz NMR) |
|---|---|
| 1 | 1.15–1.82(m, 18H, 9×CH$_2$), 2.25(s, 3H, CH$_3$), 2.35(t, 2H, CH$_2$), 2.56(s, 3H, CH$_3$), 2.96(t, 2H, CH$_2$), 6.09(s, 1H, ArH), 6.30(d, 1H, ArH), 6.90(d, 1H, ArH), 7.07(s, 1H, ArCH=) |
| 2 | 1.10–1.82(m, 18H, 9×CH$_2$), 2.38(t, 2H, CH$_2$), 2.64(s, 3H, CH$_3$), 3.00(t, 2H, CH$_2$), 6.27(d, 1H, ArH), 6.35(d, 1H, ArH), 6.96(d, 1H, ArH), 7.00(d, 1H, ArH), 7.07(s, 1H, ArCH=) |
| 3 | 0.99(t, 3H, CH$_3$), 1.22–1.85(m, 24H, 12×CH$_2$), 2.37(t, 2H, CH$_2$), 3.00(t, 4H, 2×CH$_2$), 6.36(d, 2H, 2×ArH), 6.99(d, 2H, 2×ArH), 7.08(s, 1H, ArCH=) |
| 4 | 0.88(t, 3H, CH$_3$), 1.20–1.80(m, 16H, 8×CH$_2$), 2.43(t, 2H, CH$_2$), 2.99(t, 2H, CH$_2$), 3.02(t, 2H, CH$_2$), 6.34(d, 2H, 2×ArH), 6.96(d, 2H, 2×ArH), 7.07(S, 1H, ArCH=) |
| 5 | 0.89(t, 3H, CH$_3$), 1.25–1.85(m, 16H, 8×CH$_2$), 2.88(t, 2H, CH$_2$), 3.00(t, 2H, CH$_2$), 3.33(t, 2H, CH$_2$), 6.33(d, 1H, ArH), 6.38(d, 1H, ArH), 6.95(d, 1H, ArH), 7.00(d, 1H, ArH), 7.10(s, 1H, ArCH=) |
| 6 | 1.22–1.79(m, 12H, 6×CH$_2$), 2.36(t, 2H, CH$_2$), 2.41(s, 6H, 2×CH$_3$), 2.52(s, 6H, 2×CH$_3$), 2.93(t, 2H, CH$_2$), 6.05(s, 2H, 2×ArH) |
| 7 | 1.13–1.84(m, 26H, 13×CH$_2$), 2.26(s, 3H, CH$_3$), 2.39(t, 2H, CH$_2$), 2.59(s, 3H, CH$_3$), 3.00(t, 2H, CH$_2$), 6.12(s, 1H, ArH), 6.31(d, 1H, ArH), 6.93(d, 1H, ArH), 7.08(s, 1H, ArCH=) |
| 8 | 1.23–1.78(m, 18H, 9×CH$_2$), 2.35(t, 2H, CH$_2$), 3.00(t, 2H, CH$_2$), 6.40(d, 1H, ArH), 6.69(s, 1H, ArH), 7.02(d, 1H, ArH), 7.28(s, 1H, ArCH=), 7.42–757(m, 8H, 8×ArH), 7.94–8.009m, 2H, 2×ArH) |
| 9 | 1.21–1.80(m, 18H, 9×CH$_2$), 2.35(t, 2H, CH$_2$), 3.04(t, 2H, CH$_2$), 6.40(d, 1H, ArH), 6.76(s, 1H, ArH), 6.99(d, 1H, ArH), 7.00(d, 1H, ArH), 7.09(s, 1H, ArCH=), 7.16–7.18(m, 1H, ArH), 7.46(d, 1H, ArH), 8.12(d, 1H, ArH) |
| 10 | 1.12–1.82(m, 14H, 7×CH$_2$), 2.25(s, 3H, CH$_3$), 2.34(t, 2H, CH$_2$), 2.56(s, 3H, CH$_3$), 2.98(t, 2H, CH$_2$), 6.09(s, 1H, ArH), 6.28(d, 1H, ArH), 6.90(d, 1H, ArH), 7.07(s, 1H, ArCH=) |
| 11 | 1.20–1.79(m, 18H, 9×CH$_2$), 2.24(s, 3H, CH$_3$), 2.30(t, 2H, CH$_2$), 2.56(s, 3H, CH$_3$), 2.96(t, 2H, CH$_2$), 3.67(s, 3H, CH$_3$), 6.08(s, 1H, ArH), 6.29(d, 1H, ArH), 6.91(d, 1H, ArH), 7.06(s, 1H, ArCH=) |
| 12 | 1.20–1.80(m, 18H, 9×CH$_2$), 2.31(t, 2H, CH$_2$), 2.62(s, 3H, CH$_3$), 3.00(t, 2H, CH$_2$), 3.68(s, 3H, CH$_3$), 6.27(s, 1H, ArH), 6.34(s, 1H, ArH), 6.94(d, 1H, ArH), 6.97(d, 1H, ArH), 7.07(s, 1H, ArCH=) |
| 13 | 0.99(t, 3H, CH$_3$), 1.25–1.80(m, 16H, 8×CH$_2$), 2.33(t, 2H, CH$_2$), 3.00(t, 4H, 2×CH$_2$), 3.67(s, 3H, CH$_3$), 6.35(d, 2H, 2×ArH), 6.97(d, 2H, 2×ArH), 7.06(s, 1H, ArCH=) |
| 14 | 1.21–1.89(m, 16H, 8×CH$_2$), 1.90(t, 3H, CH$_3$), 2.42(t, 2H, CH$_2$), 3.00(t, 4H, 2×CH$_2$), 3.70(s, 3H, CH$_3$), 6.34(d, 2H, 2×ARH), 6.97(d, 2H, 2×ArH), 7.08(s, H, ArCH=) |
| 15 | 0.88(t, 3H, CH$_3$), 1.20–1.80(m, 16H, 8×CH$_2$), 2.78(t, 2H, CH$_2$), 3.00(t, 2H, CH$_2$), 3.32(t, 2H, CH$_2$), 3.72(s, 3H, CH$_3$), 6.32(d, 1H, ArH), 6.37(d, 1H, ArH), 6.94(d, 1H, ArH), 7.00(d, 1H, ArH), 7.09(s, 1H, ArCH=) |
| 16 | 1.20–1.72(m, 12H, 6×CH$_2$), 2.31(t, 2H, CH$_2$), 2.41(s, 6H, 2×CH$_3$), 2.51(s, 6H, 2×CH$_3$), 2.96(t, 2H, CH$_2$), 3.67(s, 3H, CH$_3$), 6.06(s, 2H, 2×ArH) |
| 17 | 1.15–1.81(m, 26H, 13×CH$_2$), 2.29(s, 3H, CH$_3$), 2.34(t, 2H, CH$_2$), 2.60(s, 3H, CH$_3$), 3.00(t, 2H, CH$_2$), 3.71(s, 3H, CH$_3$), 6.11(s, 1H, ArH), 6.32(d, 1H, ArH), 6.95(d, 1H, ArH), 7.09(s, 1H, ArCH=) |
| 18 | 1.25–1.76(m, 18H, 9×CH$_2$), 2.31(t, 2H, CH$_2$), 3.00(t, 2H, CH$_2$), 3.67(s, 3H, CH$_3$), 6.40(d, 1H, ArH), 6.69(s, 1H, ArH), 7.03(d, 1H, ArH), 7.28(s, 1H, ArCH=), 7.41–7.56(m, 8H, 8×ArH), 7.94–7.98(m, 2H, 2×ArH). |
| 19 | 1.23–1.80(m, 18H, 9×CH$_2$), 2.30(t, 2H, CH$_2$), 3.04(t, 2H, CH$_2$), 3.67(s, 3H, CH$_3$), 6.40(d, 1H, ArH), 6.76(d, 1H, ArH), 6.98(d, 1H, ArH), 7.00(d, 1H, ArH), 7.09(s, 1H, ArCH=), 7.16–7.19(m, 1H, ArH), 7.46(d, 1H, ArH), 8.12(d, 1H, ArH). |
| 20 | 1.20–1.72(m, 16H, 8×CH$_2$), 2.21(s, 3H, CH$_3$), 2.54(s, 3H, CH$_3$), 2.98(t, 2H, CH$_2$), 3.61(t, 2H, CH$_2$), 6.06(s, 1H, ArH), 6.26(d, 1H, ArH), 6.88(d, 1H, ArH), 7.04(s, 1H, ArCH=) |
| 22 | 1.10–1.74(m, 36H, 18×CH$_2$), 2.31(t, 2H, CH$_2$), 2.35(t, 2H, CH$_2$), 3.00(t, 4H, 2×CH$_2$), 3.67(s, 3H, CH$_3$), 6.32(d, 2H, 2×ArH), 6.95(d, 2H, 2×ArH), 7.07(s, 1H, ArCH=) |
| 23 | 1.20–1.80(m, 36H, 18×CH$_2$), 2.30(t, 4H, 2×CH$_2$), 2.99(t, 4H, 2×CH$_2$), 3.67(s, 6H, 2×CH$_3$), 6.32(d, 2H, 2×ArH), 6.95(d, 2H, 2×ArH), 7.07(s, 1H, ArCH=) |
| 24 | 0.90(t, 6H, 2×CH$_3$), 1.20–1.80(m, 32H, 16×CH$_2$), 3.01(t, 4H, 2×CH$_2$), 6.34(d, 2H, 2×ArH), 6.96(d, 2H, 2×ArH), 7.08(s, 1H, ArCH=) |
| 25 | 1.20–1.86(m, 24H, 12×CH$_2$), 1.90(t, 6H, 2×CH$_3$), 3.01(t, 4H, 2×CH$_2$), 6.33(d, 2H, 2×ArH), 6.98(d, 2H, 2×ArH), 7.08(s, 1H, ArCH=) |
| 26 | 0.99(t, 6H, 2×CH$_3$), 1.40–1.80(m, 8H, 4×CH$_2$), 3.01(t, 4H, 2×CH$_2$), 6.36(d, 2H, 2×ArH), 6.98(d, 2H, 2×ArH), 7.07(s, 1H, ArCH=) |
| 27 | 1.13–1.80(m, 24H, 12×CH$_2$), 2.30(t, 4H, 2×CH$_2$), 3.00(t, 4H, 2×CH$_2$), 3.74(s, 6H, 2×CH$_3$), 6.30(d, 2H, 2×ArH), 6.97(d, 2H, 2×ArH), 7.08(s, 1H, ArCH=) |

Figure 1:
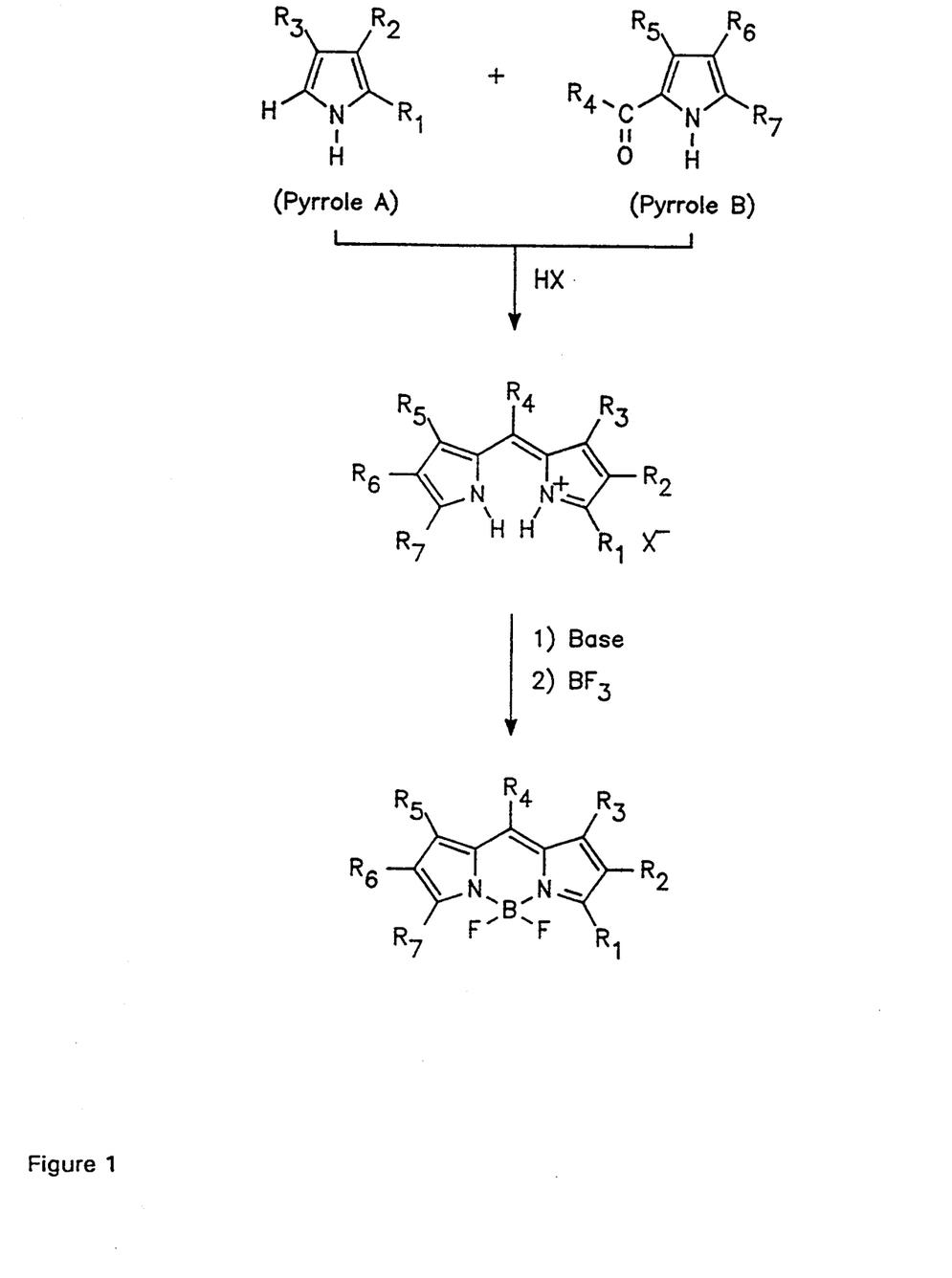
FIG. 1 shows a general reaction scheme for synthesis of BDY fatty acids.
Figure 2:
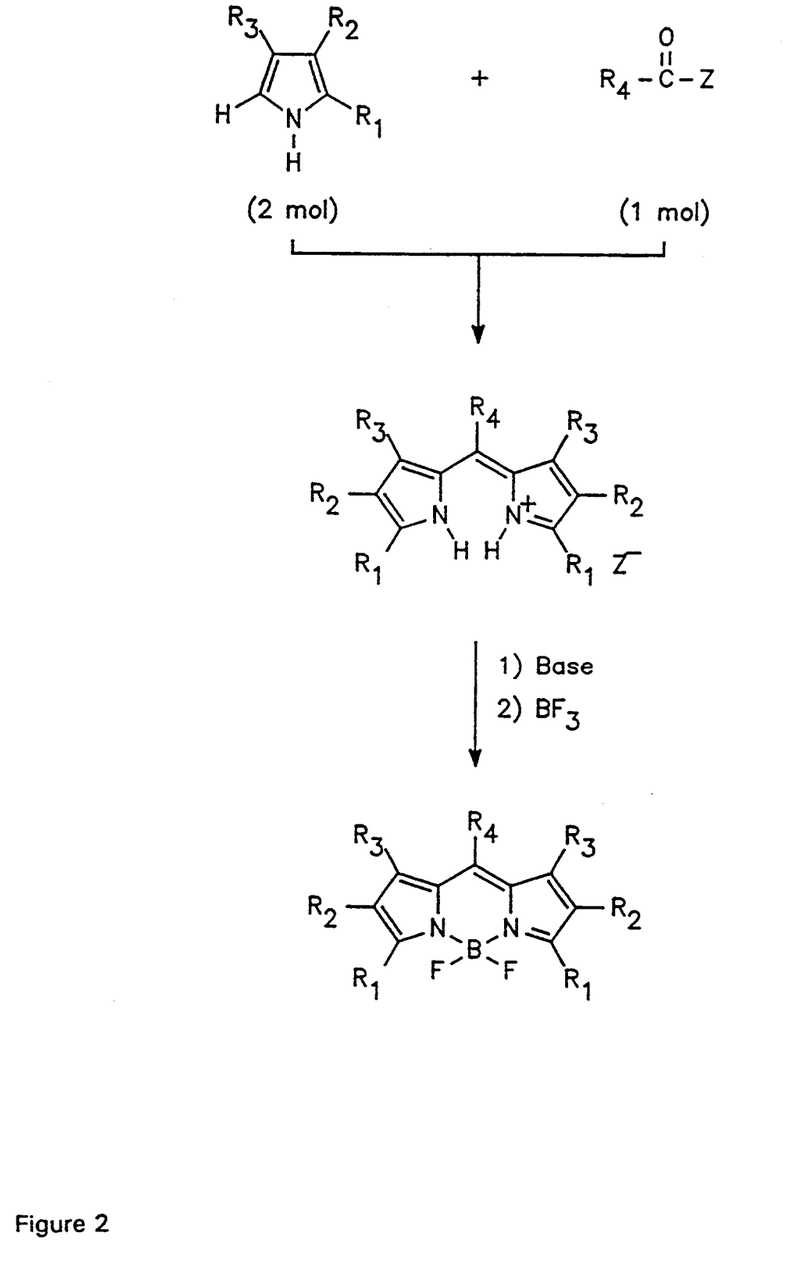
FIG. 2 shows a general reaction scheme for symmetrically substituted BDY fatty acids.

A general method of synthesis of BDY fatty acids from pyrrole intermediates is given in FIG. 1. The substituents $R_1$ to $R_7$ on the intermediates are as described above except that at least one of the substituents $R_1$ to $R_7$ is a carboxy-terminated fatty alkyl residue or a protected carboxy-terminated fatty alkyl residue or a precurcor to a carboxy-terminated fatty alkyl residue. It will be recognized by one skilled in the art that the substituents $R_1$ to $R_7$ can, in general, be interchanged at will with the resultant products still falling within the scope of this invention. It will furthermore be obvious to one skilled in the art that modifications of one or more of the substituents $R_1$ to $R_7$ to introduce the carboxylic acid subsequent to Step 2 (in which case the residue would contain one less carbon (i.e. 4–21 carbons) in the intermediate than in the final product) fall within the scope of this application. Modifications that introduce the carboxylic acid in the form of a protected derivative that is subsequently converted to a carboxylic acid also fall within the scope of this application.

In the synthesis outlined in FIG. 1, the key intermediates are two derivatives of pyrrole or a substituted pyrrole. The nitrogen of both pyrrole components must be substituted by hydrogen atoms. Pyrrole A has three substituents $R_1$, $R_2$, $R_3$ as defined above, one of which may be a fatty acid or precursor to a fatty acid. The 2-position of pyrrole A must be substituted by a hydrogen atom. Pyrrole B contains three substituents as defined above, one of which may be a fatty acid or precursor to a fatty acid. Pyrrole B must be further substituted at the 2-position by an aldehyde or ketone function —(C=O)—$R_4$. The substituents permitted as $R_4$ are as defined above and $R_4$ may be a fatty acid or precursor to a fatty acid. Tables 4 and 5 describe some pyrrole fatty acid intermediates useful for the synthesis of the representative compounds described in Tables 1–3.

TABLE 4
EXAMPLES OF PYRROLE FATTY ACID INTERMEDIATES

| #* | $R_1$ | $R_2$ | $R_3$ | $R_4$ |
|---|---|---|---|---|
| 28 | $(CH_2)_{11}CO_2CH_3$ | H | H | H |

TABLE 4-continued
EXAMPLES OF PYRROLE FATTY ACID INTERMEDIATES

| #* | $R_1$ | $R_2$ | $R_3$ | $R_4$ |
|---|---|---|---|---|
| 29 | $(CH_2)_8CO_2CH_3$ | H | H | H |
| 30 | $(CH_2)_4CO_2CH_3$ | H | H | H |
| 31 | $(CH_2)_2CO_2CH_3$ | H | H | H |
| 32 | $C(=O)(CH_2)_8CO_2CH_3$ | H | H | H |
| 33 | $(CH_2)_{15}CO_2CH_3$ | H | H | H |
| 34 | $(CH_2)_{10}OH$ | H | H | H |
| 35 | $(CH_2)_9CH_3$ | H | H | H |
| 36 | $(CH_2)_7CH_3$ | H | H | H |
| 37 | $(CH_2)_3CH_3$ | H | H | H |
| 38 | CHO | H | H | $(CH_2)_9CH_3$ |
| 39 | CHO | H | H | $(CH_2)_7CH_3$ |
| 40 | CHO | H | H | $(CH_2)_3CH_3$ |
| 41 | 2-(1-Naphthyl)ethyl | H | H | H |
| 42 | 2-(1-Naphthyl)ethyl | H | H | CHO |

*Substituents $R_1$–$R_4$ only refer to the pyrrole structure in this Table, and may not always coincide with the description in the text.

TABLE 5
M.P. AND $^1$H-NMR SPECTRAL DATA OF PYRROLE FATTY ACID INTERMEDIATES

| # | M.P. (°C.) | Chemical shift in ppm in CDCl$_3$ (300 MHz NMR) |
|---|---|---|
| 28 | 45–47 | 1.16–1.75(m, 18H, 9×CH$_2$), 2.32(t, 2H, CH$_2$), 2.60(t, 2H, CH$_2$), 3.68(s, 3H, CH$_3$), 5.92(d, 1H, ArH), 6.12(m, 1H, ArH), 6.79(d, 1H, ArH), 7.97(bs, 1H, NH) |
| 29 | 40–42 | 1.15–1.80(m, 12H, 6×CH$_2$), 2.31(t, 2H, CH$_2$), 2.60(t, 2H, CH$_2$), 3.70(s, 3H, CH$_3$), 5.90(d, 1H, ArH), 6.12(m, 1H, ArH), 6.68(d, 1H, ArH), 8.01(bs, 1H, NH) |
| 30 | 40–41 | 1.50–1.83(m, 4H, 2×CH$_2$), 2.35(t, 2H, CH$_2$), 2.61(t, 2H, CH$_2$), 3.72(s, 3H, CH$_3$), 5.90(d, 1H, ArH), 6.12(m, 1H, ArH), 6.65(d, 1H, ArH), 8.31(bs, 1H, NH) |
| 31 | oil | 2.64(t, 2H, CH$_2$), 2.92(t, 2H, CH$_2$), 3.71(s, 3H, CH$_3$), 5.93(d, 1H, ArH), 6.12(m, 1H, ArH), 6.68(d, 1H, ArH), 8.62(bs, 1H, NH) |
| 32 | 63–64 | 1.25–1.80(m, 12H, 6×CH$_2$), 2.32(t, 2H, CH$_2$), 2.79(t, 2H, CH$_2$), 3.71(s, 3H, CH$_3$), 6.30(m, 1H, ArH), 6.87(d, 1H, ArH), 7.05(d, 1H, ArH), 9.75(bs, 1H, NH) |
| 33 | 62–65 | 1.10–1.80(m, 26H, 13×CH$_2$), 2.29(t, 2H, CH$_2$), 2.58(t, 2H, CH$_2$), 3.65(s, 3H, CH$_3$), 5.90(d, 1H, ArH), 6.08(m, 1H, ArH), 6.67(d, 1H ArH), 7.98(bs, 1H, NH) |
| 34 | 57–58 | 1.20–1.75(m, 16H, 8×CH$_2$), 2.60(t, 2H, CH$_2$), 3.65(t, 2H, CH$_2$), 5.90(d, 1H, ArH), 6.13(m, 1H, ArH), 6.68(d, 1H, ArH), 7.95(bs, 1H, NH) |
| 35 | oil | 0.94(t, 3H, CH$_3$), 1.00–1.70(m, 16H, 8×CH$_2$), 2.63(t, 2H, CH$_2$), 5.96(d, 1H, ArH), 6.18(m, 1H, ArH), 6.69(d, 1H, ArH), 7.99(bs, 1H, NH) |
| 36 | oil | 0.90(t, 3H, CH$_3$), 1.08–1.72(m, 12H, 6×CH$_2$), 2.64(t, 2H, CH$_2$), 5.93(d, 1H, ArH), 6.17(m, 1H, ArH), 6.66(d, 1H, ArH), 7.93(bs, 1H, NH) |
| 37 | oil | 1.05(t, 3H, CH$_3$), 1.49–1.75(m, 4H, 2×CH$_2$), 2.70(t, 2H, CH$_2$), 6.05(d, 1H, ArH), 6.25(m, 1H, ArH), 6.70(d, 1H, ArH), 7.97(bs, 1H, NH) |
| 38 | 43–44 | 0.89(t, 3H, CH$_3$), 1.25–1.75(m, 16H, 8×CH$_2$), 2.70(t, 2H, CH$_2$), 6.09(d, 1H, ArH), 6.92(d, 1H, ArH), 9.37(s, 1H, CHO), 10.37(bs, 1H, NH) |
| 39 | 28–30 | 0.86(t, 3H, CH$_3$), 1.15–1.75(m, 12H, 6×CH$_2$), 2.72(t, 2H, CH$_2$), 6.11(d, 1H, ArH), 6.96(d, 1H, ArH), 9.39(s, 1H, CHO), 10.94(bs, 1H, NH) |
| 40 | 37–39 | 0.88(t, 3H, CH$_3$), 1.48–1.76(m, 4H, 2×CH$_2$), 2.71(t, 2H, CH$_2$), 6.07(d, 1H, ArH), 6.94(d, 1H, ArH), 9.34(s, 1H, CHO), 10.12(bs, 1H, NH) |
| 41 | oil | 3.07(t, 2H, CH$_2$), 3.42(t, 2H, CH$_2$), 6.05–6.09(m, 1H, ArH), 6.16–6.20(m, 1H, ArH), 6.63–6.67(m, 1H, ArH), 7.32(d, 1H, ArH), 7.39(t, 1H, ArH), 7.47–7.55(m, 2H, ArH), 7.75(d, 1H, ArH), 7.88(d, 1H, ArH), 8.06(d, 1H, ArH) |
| 42 | 117–118 | 3.13(t, 2H, CH$_2$), 3.45(t, 2H, CH$_2$), 6.15(d, 1H, ArH), 6.93(d, 1H, ArH), 7.30(d, 1H, ArH), 7.04(t, 1H, ArH), 7.48–7.57(m, 2H, ArH), 7.76(d, 1H, ArH), 7.88(d, 1H, ArH), 8.07(d, 1H, ArH), 9.38(s, 1H, CHO) |

Appropriately substituted derivatives of Pyrrole A and Pyrrole B may be synthesized by methods known in the art, for example as described in R. ELDERFIELD, HETEROCYCLIC COMPOUNDS, vol. 1, ch. 6, *The Chemistry of Pyrrole and Its Derivatives*, by Corwin (1950). Pyrrole fatty acids are most conveniently prepared by the Wittig reaction of pyrrole aldehydes with carboxy or protected-carboxy terminated phosphonium or phosphonate derivatives (Examples 14, 15). Fatty alkyl-substituted pyrrole derivatives have been similarly synthesized (Example 14, 15). Pyrrole B derivatives containing aldehyde substituents at position 2 (in which case $R_4$ is H) are readily prepared directly from appropriately substituted pyrroles using the Vilsmeie-Haack reaction of pyrroles that are substituted by hydrogen at the 2-position (Example 18). Pyrrole B derivatives substituted by a ketone in position 2 are readily prepared by several routes of which the reaction of a pyrrole or a nitrogen-protected derivative of a pyrrole with an acid halide or similar derivative under Friedel-Crafts conditions is probably the most versatile (Example 16).

Synthesis of heteroaryl-substituted BDY fluorophores is described in co-pending application Heteroaryl-Substituted Dipyrromethaneboron Difluoride Dyes and Methods for Their Synthesis, filed by inventors Haugland and Kang on Dec. 18, 1990 (the specification of which is incorporated herein by reference). The heteroaryl-substituted intermediates can be used to synthesize BDY fatty acids that contain heteroaryl substituents (Example 11).

Symmetrically substituted BDY fatty derivatives containing a non-hydrogen substituent at $R_4$ are most conveniently synthesized by the direct reaction of at least 2 moles of Pyrrole A per mole of an anhydride or acid halide in a "one-pot" reaction (Example 8). In this case it is not necessary to isolate the 2-ketopyrrole intermediate. If the acid halide component in this reaction is a half acid chloride, half ester derivative of an aliphatic diacid or a cyclic anhydride of a diacid, the resultant $R_4$ is readily converted to a subject BDY fatty acid (Example 13).

Examples are provided of general methods for synthesis of the subject dyes. It will be realized by one skilled in the art that modifications of the reactants and conditions can be made that fall within the scope of this invention. In general, to synthesize the subject dyes, Pyrrole A and Pyrrole B are condensed in an acid-mediated reaction (Examples 3, 4, 5, 6, 7, 9, 10, 11 and 12) to a dipyrromethene intermediate. This product may be isolated or used without isolation. The dipyrromethene intermediate is converted to a fluorescent BDY product by $BF_3$ or a complex of $BF_3$ such as its complex with ether or tetrahydrofuran in combination with a suitable base. Suitable bases include but are not limited to: triethylamine, N,N-diisopropylethylamine, 1,8-bis(dimethylamino)naphthalene, tetramethylenediamine, dizabicyclooctane, diazabicycloundecene, 4-dimethylaminopyridine and 4-pyrrolidinopyridine. If required, substituents in $R_1$ to $R_7$ can be converted to the free carboxylic acids by well recognized methods that include hydrolysis of esters (Example 1) and oxidation of alcohols (Example 2).

The following examples of the synthesis and characterization of the BDY fatty acids and their intermediates is intended to illustrate the generality of the invention and not to define or limit the scope of the invention.

EXAMPLE 1

4,4-Difluoro-5,7-dimethyl-3-(11-carboxyundecyl)-4-bora-3a,4a-diaza-s-indacene (Compound 1)

To a solution of 0.60 g (1.39 mmol) of compound 11 in 150 mL of tetrahydrofuran were added 30 mL of water and 3 mL of 85% phosphoric acid and the whole mixture was heated under reflux for 4 days. After cooling to room temperature, the reaction mixture was concentrated under reduced pressure to remove most of tetrahydrofuran. The resulting aqueous residue was extracted with chloroform. The chloroform layer was dried over anhydrous sodium sulfate and concentrated under reduced pressure to give an orange red oil. The crude product was subjected to silica gel column chromatography. It was first eluted with dichloromethane to give 0.16 g of an unreacted starting material 11. It was then eluted with 10% methanol in dichloromethane to afford 0.36 g (62% yield) of compound 1 as an orange red solid.

Compounds 2, 3, 4, 5, 6, 7, 8 and 9 were prepared by hydrolysis of esters 12, 13, 14, 15, 16, 17 and 18, respectively, as described in the preparation of compound 1. Considering the recovered unreacted starting materials, yields are as follows: 2 (70%), 3 (79%), 4 (80%), 5 (48%), 6 (59%), 7 (57%), 8 (72%) and 9 (68%).

EXAMPLE 2

3-(9-Carboxynonyl)-4,4-difluoro-5,7-dimethyl-4-bora-3a,4a-diaza-s-indacene (Compound 10)

A mixture of 23 mg (0.06 mmol) of compound 20 and 80 mg (0.21 mmol) of pyridinium dichromate in 300 μL of dry dimethylformamide was stirred at room temperature for 15 hours. The reaction mixture was diluted with 10 mL of water and the product was extracted with ethyl acetate (3×10 mL). The combined extracts were dried over anhydrous sodium sulfate and concentrated under reduced pressure to give an orange oil. The crude product was purified by silica gel column chromatography (initial eluant; dichloromethane, final eluant; 5% methanol in chloroform) to give 2 mg (10%) of compound 10 as an orange red solid.

EXAMPLE 3

4,4-Difluoro-5,7-dimethyl-3-(11-methoxycarbonylundecyl)-4-bora-3a,4a-diaza-s-indacene (Compound 11)

To a solution of 0.88 g (7.15 mmol) of 2,4-dimethylpyrrole-5-carboxaldehyde and 2.00 g (7.16 mmol) of methyl 2-pyrroledodecanoate, 28, in 25 mL of ethanol was added 1.2 mL (10.6 mmol) of 48% hydrobromic acid while the reaction mixture was stirred vigorously in an ice bath. After stirring in an ice bath for 1 hour, the resulting orange precipitate was collected by filtration to give 2.90 g of an orange solid as a dipyrromethene intermediate. It was then dissolved in 150 mL of dichloromethane and to this solution was added 3.90 g (18.2 mmol) of 1,8-bis(dimethylamino)naphthalene, followed by addition of 2.8 mL (22.8 mmol) of boron trifluoride etherate. After stirring at room temperature for 3 hours, the resulting precipitate was removed by filtration and the filtrate was concentrated under reduced pressure to give an orange brown oil. This crude product was purified by silica gel column chromatography with dichloromethane as eluant to give 2.20 g (71%) of compound 11 as an orange red solid.

EXAMPLE 4

4,4-Difluoro-5-methyl-3-(11-methoxycarbonylundecyl)-4-bora-3a,4a-diaza-s-indacene (Compound 12)

To a solution of 1.00 g (3.6 mmol) of methyl 2-pyrroledodecanoate, 28, and 0.39 g (3.6 mmol) of 5-methylpyrrole-2-carboxaldehyde in 30 mL of dichloromethane and 30 mL of hexane was added 320 μL (3.7 mmol) of phosphorus oxychloride while the reaction mixture was stirred vigorously in an ice bath. The reaction mixture was stirred in an ice bath for 2 hours and to this was added 3.2 g (14.9 mmol) of 1,8-bis(dimethylamino)naphthalene, followed by addition of 2.5 mL (20.3 mmol) of boron trifluoride etherate. After the whole mixture was stirred at room temperature for 3 hours, the resulting precipitate was filtered off and the filtrate was concentrated under reduced pressure to give an orange brown oil. The crude product was purified by silica gel column chromatography with dichloromethane as eluant to afford 0.78 g (52%) of compound 12 as an orange red solid. From this reaction, compound 23 was also isolated as a by-product (40 mg, 2%).

EXAMPLE 5

4,4-Difluoro-5-butyl-3-(8-methoxycarbonyloctyl)-4-bora-3a,4a-diaza-s-indacene (Compound 13)

This was prepared in the same manner as described in EXAMPLE 4 from 5-butylpyrrole-2-carboxaldehyde, 40 (1.0 g, 6.6 mmol) and methyl 2-pyrrolenonanoate, 29 (1.57 g, 6.6 mmol). The product 13 (1.15 g, 42%) was obtained as an orange red solid. From this reaction, compound 26 (135 mg, 7%) and compound 27 (20 mg, 0.6%) were also isolated as by-products.

EXAMPLE 6

4,4-Difluoro-5-octyl-3-(4-methoxycarbonylbutyl)-4-bora-3a,4a-diaza-s-indacene (Compound 14)

This was prepared in the same manner as described in EXAMPLE 4 from 5-octylpyrrole-2-carboxaldehyde, 39, (1.33 g, 6.4 mmol) and methyl 2-pyrrolepentanoate, 30, (1.17 g, 6.4 mmol). The product, 14, (1.16 g, 43%) was obtained as an orange red solid. From this reaction compound 25 (133 mg, 5%) was also isolated as a by-product.

EXAMPLE 7

5-Decyl-4,4-difluoro-3-(2-methoxycarbonylethyl)-4-bora-3a,4a-diaza-s-indacene (Compound 15)

This was prepared in the same manner as described in EXAMPLE 4 from 5-decylpyrrole-2-carboxaldehyde 38 (1.5 g, 6.37 mmol) and methyl 2-pyrrolepropionate 31 (0.98 g, 6.39 mmol). The product 15 (0.73 g, 27%) was obtained as an orange red solid. From this reaction, compound 24 (242 mg, 8%) was also isolated as a by-product.

EXAMPLE 8

4,4-Difluoro-1,3,5,7-tetramethyl-8-(8-methoxycarbonyloctyl)-4-bora-3a,4a-diaza-s-indacene (Compound 16)

To a solution of 2,4-dimethylpyrrole (1.20 g, 12.6 mmol) in 10 mL of dichloromethane was added dropwise a solution of 9-methoxycarbonylnonanoyl chloride (1.48 g, 6.3 mmol) in 5 mL of dichloromethane while the reaction mixture was stirred in an ice bath. The reaction mixture was stirred at room temperature for 16 hours and was added 4.0 g (18.6 mmol) of 1,8-bis(dismethylamino)naphthalene, followed by addition of 2.7 mL (21.9 mmol) of boron trifluoride etherate. After the whole reaction mixture was stirred at room temperature for 2 hours, the resulting precipitate was removed by filtration and the filtrate was concentrated under reduced pressure. The crude product was purified by silica gel column chromatography with dichloromethane as eluant to give 0.35 g (13) of compound 16 as an orange red solid.

EXAMPLE 9

4,4-Difluoro-5,7-dimethyl-3-(15-methoxycarbonylpentadecyl)-4-bora-3a,4a-diaza-s-indacene (Compound 17)

This was prepared in the same manner as described in EXAMPLE 4 from methyl 2-pyrrolehexadecanoate, 33 (1.50 g, 4.5 mmol) and 3,5-dimethylpyrrole-2-carboxaldehyde (0.55 g, 4.5 mmol). The product, 17 (1.20 g, 55%) was obtained as an orange red solid.

EXAMPLE 10

4,4-Difluoro-5,7,-diphenyl-3-(11-methoxycarbonylundecyl)-4-bora-3a,4a-diaza-s-indacene (Compound 18)

This was prepared in the same manner as described in EXAMPLE 4 from methyl 2-pyrroledodecanoate, 28 (0.50 g, 1.8 mmol) and 3,5-diphenylpyrrole-2-carboxaldehyde (0.44 g, 1.8 mmol). The product, 18 (0.37 g, 38%) was obtained as an orange red oil. The 3,5-diphenylpyrrole-2-carboxaldehyde needed for this synthesis was prepared from 2,4-diphenylpyrrole by the Vilsmeier Haack formylation. The 2,4-diphenylpyrrole was prepared as described in C.F.H. Allen et al., ORG. SYNTH. COLL. Vol. III, p. 33.

EXAMPLE 11

4,4-Difluoro-5-thienyl-3-(11-methoxycarbonylundecyl)-4-bora-3a,4a-diaza-s-indacene (Compound 19)

This was prepared in the same manner as described in EXAMPLE 4 from methyl 2-pyrroledodecanoate, 28 (0.50 g, 1.8 mmol) and 5-(2-thienyl)pyrrole-2-carboxaldehyde (0.32 g, 1.8 mmol). The product, 19 (0.36 g, 42%) was obtained as a red solid. The 2-(2-thienyl)pyrrole needed for this synthesis was prepared as described in C. G. Kruse, et al., HETEROCYCLES 26, 3141 (1987).

EXAMPLE 12

4,4-Difluoro-5,7-dimethyl-3-(10-hydroxydecyl)-4-bora-3a,4a-diaza-s-indacene (Compound 20)

This was prepared in the same manner as described in EXAMPLE 3 from 2,4-dimethylpyrrole-5-carboxaldehyde (110 mg, 0.9 mmol) and 2-(10-hydroxydecyl)pyrrole (200 mg, 0.9 mmol), 34. The product 20 (152 mg, 45%) was obtained as an orange red oil.

EXAMPLE 13

3,5-Bis(11-carboxyundecyl)-4,4-difluoro-4-bora-3a,4a-diaza-s-indacene, (Compound 21) and 3-(11-carboxyundecyl)-4,4-difluoro-5-(11-methoxycarbonyl)-4-bora-3a,4a-diaza-s-indacene, (Compound 22)

To a solution of 90 mg (0.15 mmol) of compound 23 in 15 mL of tetrahydrofuran was added 5 mL of water, followed by addition of 0.5 mL of 85% phosphoric acid and the mixture was heated under reflux for 4 days. After cooling to room temperature, the reaction mixture was concentrated under reduced pressure to remove most of tetrahydrofuran. The remaining aqueous residue was extracted with chloroform. The combined extracts were dried over anhydrous sodium sulfate and concentrated under reduced pressure to give an orange red solid. It was subjected to purification by silica gel column chromatography. It was first eluted with 5% methanol in chloroform to give 10 mg (11%) of compound 22 as an orange red solid. It was then eluted with 20% methanol in chloroform to afford 29 mg (34%) of compound 21 as an orange red solid.

EXAMPLE 14

Methyl 2-pyrroledodecanoate (Compound 28)

To a stirred solution of sodium (0.80 g, 34.8 mmol) in 10 mL of methanol was added a solution of 10-methoxycarbonyldecyltriphenylphosphonium bromide (18 g, 33.2 mmol) in 120 mL of dry tetrahydrofuran at room temperature over a period of 30 minutes under a nitrogen atmosphere. After addition of a solution of pyrrole-2-carboxaldehyde (2.88 g, 30.3 mmol) in 30 mL of dry tetrahydrofuran, the reaction mixture was heated at reflux under a nitrogen atmosphere for 20 hours. After cooling to room temperature, the reaction mixture was filtered through a diatomaceous earth pad and the filtrate was concentrated under vacuum to give a yellow oil. This was purified by silica gel column chromatography with elution by a mixture of ethyl acetate and hexane (1:9) to give 6.1 g of a pale yellow oil as a mixture of cis- and trans-11'-methoxycarbonyl-1-(2-pyrrolyl)undec-1-ene. It was then dissolved in a mixture of dichloromethane (15 mL) and methanol (100 mL) in a Parr shaker bottle and to this was added 700 mg of 10% palladium on charcoal. The mixture was pressurized to 50 psi with hydrogen and shaken at room temperature for 2 hours. The reaction mixture was filtered through a diatomaceous earth pad and the filtrate was concentrated under vacuum to give 6.0 g (73%) of compound 28 as an off white solid.

* 10-Methoxycarbonyldecyltriphenylphosphonium bromide was prepared by the procedure of B. Katusin-Razem [Croatica Chimica Acta 51, 163 (1978)].

* Compounds 29, 30, 33, 35, 36, 37 and 41 were prepared by methods similar to those used to prepare 28 by reaction of pyrrole-2-carboxaldehyde and the corresponding phosphonium bromide followed by catalytic hydrogenation.

EXAMPLE 15

Methyl 2-pyrrolepropionate (Compound 3)

A solution of pyrrole-2-carboxaldehyde (3.9 g, 41 mmol) and carbomethoxymethylenetriphenylphosphorane (14 g, 42 mmol) in 160 mL of dry benzene was heated at reflux for 18 hours under a nitrogen atmosphere. After cooling, the reaction mixture was concentrated under vacuum and the resulting oil was purified by silica gel column chromatography eluting with a mixture of ethyl acetate and hexanes (1:9) to give 5.11 g of a mixture of cis- and trans-methyl 2-(2-pyrrolyl)acrylate. It was then dissolved in 100 mL of methanol in a Parr shaker bottle and to this was added 500 mg 10% palladium on charcoal. The mixture was pressurized to 50 psi with hydrogen and shaken at room temperature for 2 hours. The reaction mixture was filtered through a diatomaceous earth pad and the filtrate was concentrated under vacuum to give 5.10 g (82%) of compound 31 as a pale yellow oil.

EXAMPLE 16

9-Methoxycarbonyl-2-nonanoylpyrrole (Compound 32)

A mixture of methyl hydrogen sebacate (4.0 g, 18.5 mmol), 2,2'-dipyridyldisulfide (6.1 g, 27.7 mmol) and triphenylphosphine (7.3 g, 27.5 mmol) in 30 mL of dry toluene was stirred at room temperature under argon for 1 day. The reaction mixture was cooled to −78° C. and dropwise treated with pyrrylmagnesium chloride (prepared from 20 mL, 3.0M methylmagnesium chloride in tetrahydrofuran and 4.1 g (61.1 mmol) of pyrrole in 180 mL of toluene at −40° C. by the method of K. C. Nicolaou, et al [Tetrahedron Letters 22, 4647 (1981)]. After stirring at −78° C. for 1 hour, the reaction mixture was quenched with 200 mL of saturated aqueous ammonium chloride solution and extracted with three portions of 200 mL of ether. The combined ether extracts were washed with 5% aqueous potassium carbonate (3×200 mL), water (3×200 mL) and finally with brine (3×200 mL). The organic layer was separated, dried over anhydrous sodium sulfate and concentrated under vacuum to give a thick oil. This crude product was purified by silica gel column chromatography eluting with 3:1 ethyl acetate/hexanes to give 3.9 g (80%) of compound 32 as a white solid.

EXAMPLE 17

2-(10-Hydroxydecyl)pyrrole (Compound 34)

To a suspension of 400 mg (10.5 mmol) of lithium aluminum hydride in 10 mL of dry ether was added a solution of 700 mg (2.6 mmol) of 9-methoxycarbonyl-2-nonanoylpyrrole, 32, over a period of 10 minutes while the reaction mixture was cooled in an ice bath under a nitrogen atmosphere. The reaction mixture was heated under reflux for 15 hours and then cooled on an ice bath. The excess hydride was carefully decomposed by slow addition of 0.4 mL water, 0.4 mL of 15% aqueous sodium hydroxide and finally 2.4 mL water. After addition of 100 mL of ether, the whole mixture was stirred for 30 minutes. It was filtered and the inorganic residue was washed several times with ether. The combined filtrate was dried over anhydrous sodium sulfate, then filtered and concentrated under vacuum. The crude product was purified by silica gel column chromatography with 1:5 ethyl acetate/hexanes as eluant, giving 450 mg (76%) of compound 34 as a white solid.

EXAMPLE 18

5-Decylpyrrole-2-carboxaldehyde (Compound 38)

To an ice cooled 4 g (56 mmol) of dimethylformamide was added 8.6 g (56 mmol) of phosphorous oxychloride over a period of 15 minutes while stirring under a nitrogen atmosphere. The mixture was stirred 15 minutes and then 15 mL of 1,2-dichloroethane was added. To this mixture was added a solution of 10.5 g (50.6 mmol) of 2-decylpyrrole, 35, in 15 mL of 1,2-dichloroethane while cooling in an ice bath. The reaction mixture was then heated under reflux for 15 minutes, during which time there was copious evolution of hydrogen chloride gas. After cooling to room temperature, a solution of sodium acetate trihydrate (38.1 g, 280 mmol) in 50 mL of water was added to the mixture. After heating at reflux for 15 minutes, the mixture was cooled and the 1,2-dichloroethane layer was separated. The aqueous layer was extracted with chloroform. The combined organic extracts were washed with saturated aqueous sodium carbonate solution and dried over anhydrous sodium carbonate. Following evaporation of solvent under vacuum, the crude product was purified by silica gel column chromatography with 1:9 ethyl acetate/hexanes as eluant, giving 9.8 g (82%) of compound 38 as a white solid.

* Compounds 39, 40 and 42 were prepared from compounds 36, 37 and 41, respectively, by the method used to prepare compound 38.

What is claimed is:

1. A compound of the formula:

wherein at least one of substituents $R_1$, $R_2$, $R_3$, $R_4$, $R_5$, $R_6$ and $R_7$ is a carboxylic acid terminated residue, wherein said residue is a linear hydrocarbon chain that is fully saturated or unsaturated, or contains one or more branches, again being saturated or unsaturated, said substituent containing 5 to 22 carbon atoms;

wherein at least one of substituents $R_1$, $R_2$, $R_3$, $R_5$, $R_6$ and $R_7$ is an aryl or heteroaryl residue, where said aryl residue is unsubstituted phenyl, unsubstituted naphthyl, lower alkyl- or alkoxy-substituted phenyl, or lower alkyl- or alkoxy-substituted naphthyl, and where said heteroaryl residue is pyrrole, thiophene, furan, oxazole, isoxazole, oxadiazole, imidazole, benzoxazole, benzothiazole, benzimidazole, benzofuran, or indole; and the remaining substituents $R_1$, $R_2$, $R_3$, $R_4$, $R_5$, $R_6$ and $R_7$, which may be the same or different, are alkyl or arylalkyl residues containing 1 to 16 aliphatic carbon atoms, or aryl or heteroaryl residues, where said aryl residue is unsubstituted phenyl, unsubstituted naphthyl, lower alkyl- or alkoxy-substituted phenyl, or lower alkyl- or alkoxy-substituted naphthyl, and where said heteroaryl residue is pyrrole, thiophene, furan, oxazole, isoxazole, oxadiazole, imidazole, benzoxazole, benzothizole, benzimidazole, benzofuran, or indole, or H.

2. A compound, as claimed in claim 1, wherein no more than two of the substituents $R_1$, $R_2$, $R_3$, $R_4$, $R_5$, $R_6$ and $R_7$ are carboxylic acid terminated residues.

3. A compound, as claimed in claim 2, wherein the one or two carboxylic acid terminated residues is/are linear.

4. A compound, as claimed in claim 1, wherein no more than two of substituents $R_1$, $R_4$, and $R_7$ are carboxylic acid terminated residues.

5. A compound, as claimed in claim 4, wherein $R_1$ is one carboxylic acid terminated residue.

6. A compound, as claimed in claim 5, wherein said carboxylic acid terminated residue is linear and saturated.

7. A compound, as claimed in claim 4, wherein $R_4$ is one carboxylic acid terminated residue.

8. A compound, as claimed in claim 7, wherein said carboxylic acid terminated residue is linear and saturated.

9. A compound, as claimed in claim 1, wherein $R_1$, $R_2$, or $R_3$, is one carboxylic acid terminated residue and $R_5$, $R_6$, or $R_7$ is one alkyl or arylalkyl residue containing 1 to 16 aliphatic carbon atoms.

10. A compound, as claimed in claim 9, wherein $R_1$ is one carboxylic acid terminated residue and $R_7$ is one alkyl residue.

11. A compound, as claimed in claim 9, wherein one carboxylic acid terminated residue contains n carbon atoms and one alkyl or arylalkyl residue contains (13-n) aliphatic carbon atoms.

12. A compound, as claimed in claim 11, wherein $R_1$ is one carboxylic acid terminated residue containing n carbon atoms, where n is greater than 8; and $R_7$ is one alkyl residue.

13. A compound, as claimed in claim 1, wherein $R_1$, $R_2$, or $R_3$, is one carboxylic acid terminated residue; and $R_5$, $R_6$, or $R_7$ is one aryl or heteroaryl residue.

14. A compound, as claimed in claim 13, wherein $R_1$ is one carboxylic acid terminated residue and $R_7$ is one aryl or heteroaryl residue.

15. A compound, as claimed in claim 1, wherein $R_4$ is one carboxylic acid terminated residue; and $R_1$ and $R_7$, or $R_2$ and $R_6$, or $R_3$ and $R_5$, are identical alkyl or arylalkyl residues containing 1 to 16 aliphatic carbon atoms.

16. A compound, as claimed in claim 15, wherein $R_4$ is one carboxylic acid terminated residue; and $R_1$ and $R_7$ are identical alkyl or arylalkyl residues.

17. A compound, as claimed in claim 1, wherein $R_4$ is one carboxylic acid terminated residue; and $R_1$ and $R_7$, or $R_2$ and $R_6$, or $R_3$ and $R_5$, are identical aryl or heteroaryl residues.

18. A compound, as claimed in claim 17, wherein $R_4$ is one carboxylic acid terminated residue; and $R_1$ and $R_7$ are identical aryl or heteroaryl residues.

19. A compound, as claimed in claim 1, wherein $R_1$ and $R_7$ are identical;

$R_2$ and $R_6$ are identical; and $R_3$ and $R_5$ are identical.

20. A compound, as claimed in claim 19, wherein $R_4$ is one carboxylic acid terminated residue; and $R_1$ and $R_7$ are identical alkyl residues.

* * * * *